United States Patent
Westermarck et al.

(10) Patent No.: US 10,094,834 B2
(45) Date of Patent: Oct. 9, 2018

(54) METHOD OF SELECTING INDIVIDUALIZED BRAIN CANCER THERAPY

(71) Applicant: TURUN YLIOPISTO, Turun yliopisto (FI)

(72) Inventors: Jukka Westermarck, Turku (FI); Amanpreet Kaur, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 122 days.

(21) Appl. No.: 14/424,400

(22) PCT Filed: Aug. 29, 2013

(86) PCT No.: PCT/FI2013/050834
§ 371 (c)(1),
(2) Date: Feb. 26, 2015

(87) PCT Pub. No.: WO2014/033367
PCT Pub. Date: Mar. 6, 2014

(65) Prior Publication Data
US 2015/0204877 A1 Jul. 23, 2015

(30) Foreign Application Priority Data
Aug. 30, 2012 (FI) ...................................... 20125897

(51) Int. Cl.
*A61K 31/00* (2006.01)
*C12Q 1/68* (2018.01)
*C07D 413/06* (2006.01)
*G01N 33/574* (2006.01)

(52) U.S. Cl.
CPC . *G01N 33/57407* (2013.01); *G01N 2333/918* (2013.01); *G01N 2333/91011* (2013.01); *G01N 2800/52* (2013.01)

(58) Field of Classification Search
None
See application file for complete search history.

(56) References Cited

U.S. PATENT DOCUMENTS

| 2002/0107374 A1 | 8/2002 | Pallas et al. | |
|---|---|---|---|
| 2005/0245475 A1* | 11/2005 | Khvorova | A61K 31/713 514/44 A |
| 2006/0100153 A1 | 5/2006 | Shridhar et al. | |
| 2009/0182134 A1 | 7/2009 | Khvorova et al. | |
| 2009/0239244 A1 | 9/2009 | Shi et al. | |

FOREIGN PATENT DOCUMENTS

| JP | 2007-082433 A | 4/2007 |
|---|---|---|
| WO | WO 2004/096991 A2 | 11/2004 |
| WO | WO 2009/100173 A2 | 8/2009 |
| WO | WO 2011/087926 A1 | 7/2011 |
| WO | WO 2012/175798 A2 | 12/2012 |

OTHER PUBLICATIONS

Chang et al. ("Chang", Leukemia, 2003, 17, 1263-1293).*
Afanas'ev et al., "Flow cytometry and biochemical analysis of DNA degradation characteristic of two types of cell death", FEBS Letters, vol. 194, No. 2, Jan. 1986, pp. 347-350.
Cairncross et al., "Specific Genetic Predictors of Chemotherapeutic Response and Survival in Patients with Anaplastic Oligodendrogliomas", Journal of the National Cancer Institute, vol. 90, No. 19, Oct. 7, 1998, pp. 1473-1479.
Finnish Office Action and Search Report dated May 28, 2013, for Finnish Application No. 20125897.
Janssens et al., "PP2A holoenzyme assembly: in cauda venenum (the sting is in the tail)", Trends in Biochemical Sciences, vol. 33, No. 3, 2008, pp. 113-121.
Pollack et al., "Blocking of glioma proliferation in vitro and in vivo and potentiating the effects of BCNU and cisplatin: UCN-01, a selective protein kinase C inhibitor", J Neurosurg, vol. 84, Jun. 1996, p. 1024-1032.
Prosperi et al., "Nuclease-Induced DNA Structural Changes Assessed by Flow Cytometry With the Intercalating Dye Propidium Iodide", Cytometry, vol. 12, 1991, pp. 323-329.
Puustinen et al., "PME-1 Protects Extracellular Signal-Regulated Kinase Pathway Activity from Protein Phosphatase 2A-Mediated Inactivation in Human Malignant Glioma", Cancer Research, vol. 69, No. 7, Apr. 1, 2009 (Published online first Mar. 17, 2009), pp. 2870-2877.
Riccardi et al., "Analysis of apoptosis by propidium iodide staining and flow cytometry", Nature Protocols, vol. 1, No. 3, 2006 (Published online Nov. 9, 2006), pp. 1458-1461.
Sathornsumetee et al., "Molecularly Targeted Therapy for Malignant Glioma", Cancer, vol. 110, No. 1, Jul. 1, 2007 (Published online May 22, 2007), pp. 13-24.
Westermarck et al., "Multiple pathways regulated by the tumor suppressor PP2A in transformation", Trends in Molecular Medicine, vol. 14, No. 4, 2008 (Available online Mar. 10, 2008), pp. 152-160.
Xing et al., "Structural Mechanism of Demethylation and Inactivation of Protein Phosphatase 2A", Cell, vol. 133, Apr. 4, 2008, pp. 154-163.
Japanese Office Action issued in Japanese Patent Application No. 2015-529086 dated Jun. 27, 2017.

* cited by examiner

*Primary Examiner* — Mark Halvorson
*Assistant Examiner* — Kauser M Akhoon
(74) *Attorney, Agent, or Firm* — Birch, Stewart, Kolasch & Birch, LLP

(57) ABSTRACT

The present invention relates to a method of selecting individualized brain cancer therapy on the basis of the patient's PME-1 expression level in the diseased tissue.

10 Claims, 10 Drawing Sheets
Specification includes a Sequence Listing.

METHOD OF SELECTING INDIVIDUALIZED BRAIN CANCER THERAPY

FIELD OF THE INVENTION

The invention relates to the field of personalized medicine. More specifically, the invention relates to a method of selecting individualized brain cancer therapy on the basis of the patient's proteomic profile in the diseased tissue.

BACKGROUND OF THE INVENTION

Personalized medicine is a relatively young field of healthcare that aims at identifying each patient's genetic, genomic, and clinical information which allows making accurate individualized predictions of the likelihood of developing a given disease, prognosis of the disease, and susceptibility to therapy. Thus, personalized medicine enables making more informed medical decisions, choosing better-targeted therapies, and reducing healthcare costs.

Gliomas are a broad category of primary brain and spinal cord tumors with tumor cells that display characteristics of glial cells and constituting about 42% of all brain tumors. According to the American Cancer Society, gliomas can be divided into three subtypes, namely astrocytomas, oligodendrogliomas, and epedymomas, depending on the type of glial cells affected. Astrocytomas arise from astrocytes and make up about 35% of all brain tumors. Generally, astrocytomas are not curable because they spread all through the normal brain tissue. Astrocytomas are usually classified as low grade, intermediate grade, or high grade, on the basis of a microscopic examination of a biopsy sample, depending on criteria used by a doctor examining the biopsy under a microscope. The highest grade of astrocytomas is called glioblastomas the most common adult malignant brain tumor. The average survival of patients with glioblastoma multiforme (GBM) is less than 14 months after diagnosis.

Owing to the heterogeneous genomic landscape of gliomas, future therapies are likely to require personalization for each patient's tumor genotype and proteomic profile. In fact, patients with oligodendrogliomas have already benefited from personalized medicine as there is a clear relationship between response to chemotherapy and chromosomal profile (Cairncross et al., J. Natl. Cancer Inst., 1998, 90: 1473-1479).

Protein phosphatase methyltransferase 1 (PME-1) has been identified as a cancer-associated protein whose expression correlates with the progression of low-grade astrocytic gliomas to malignant glioblastomas (GBMs) (Puustinen et al., Cancer Res. 2009, 69: 2870-2877). PME-1 interacts with protein phosphatase 2A (PP2A), the inhibition of which is a prerequisite for human cell transformation (reviewed in Westermarck and Hahn, Trends Mol. Med., 2008, 14: 152-160). It has been suggested that PME-1 inhibits PP2A activity via its enzymatic methylesterase activity required for demethylation of the conserved leucine 309 on catalytic PP2Ac subunit (Janssens et al., Trends Biochem. Sci., 2008, 33:113-21). An alternative mechanism of inhibition has been proposed on the basis of structural analysis of PME-1-PP2A complex demonstrating that PME-1 directly binds to catalytic cleft of the PP2Ac subunit (Xing et al., Cell, 2008, 133:154-163). Nevertheless, the role of PME-1 in the development of gliomas and their chemoresistance is yet to be determined.

Although recent studies have found some candidate molecules as possible future targets for personalized therapeutics in the treatment of gliomas, there is also an identified need for identification and elucidation of markers that can be used to differentiate patients who a likely to benefit from chemotherapy from those who are not likely to respond to said therapy.

BRIEF DESCRIPTION OF THE INVENTION

The present invention relates to a method of selecting a brain cancer therapy for a patient in need of such therapy. The method comprises the steps of a) assessing the expression level of PME-1 in a sample obtained from said patient; b) using the results obtained in step a) as criteria for selecting a brain cancer therapy to which said patient is susceptible.

In one embodiment, increased PME-1 expression indicates that said patient is not susceptible to monotherapy with a STS derivative.

In another embodiment, increased PME-1 expression indicates that said patient is susceptible to a combination therapy with a STS derivative and a PME-1 silencing agent.

In yet another embodiment, intact PME-1 expression indicates that said patient is susceptible to cancer therapy with a STS derivative.

In a further embodiment, said STS derivative has the general Formula (I) described hereinbelow.

In a still further embodiment, said patient suffers from a brain cancer selected from a group consisting of glioma, astrocytoma, juvenile pilocytic astrocytoma, low grade astrocytoma, anaplastic astrocytoma, glioblastoma, oligodendroglioma, and ependymoma.

Other aspects, specific embodiments, objects, details, and advantages of the invention are set forth in the following drawings, detailed description and examples.

BRIEF DESCRIPTION OF THE DRAWINGS

In the following the invention will be described in greater detail by means of preferred embodiments with reference to the attached drawings, in which

FIG. 5B represent the colonogenic potential of scrambled or PME-1 specific dsRNA transfected T98G glioblastoma cells after 2 days of treatment with indicated concentration of staurosporine derivatives, PKC412 and K252a.

FIGS. 5C and 5D represent the colonogenic potential of scrambled or PME-1 specific dsRNA transfected U251 MG and U87MG glioblastoma cells respectively, after 2 days of treatment with an indicated concentration of staurosporine (STS), PKC412 and K252a.

DETAILED DESCRIPTION OF THE INVENTION

Figure 1A:
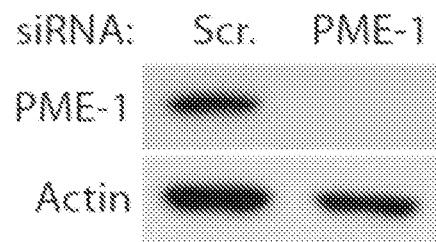
FIG. 1A is a western blot demonstrating the level of PME-1 expression in human glioblastoma T98G cells transfected with a scrambled dsRNA (Scr.) and PME-1 specific dsRNA (PME-1).

The present invention is based on a surprising finding that the level of PME-1 expression but not of another PP2A inhibitor protein, CIP2A, in glioma cells can be used for selecting a brain cancer therapy to which the patient in question is susceptible. In some embodiments, the level of PME-1 expression may be used to predict the sensitivity of the respective cancers to certain small molecule chemotherapeutic agents, namely staurosporine (STS) derivatives.

To be more specific, it has now been found out that brain cancer cells with intact levels of PME-1 expression respond statistically significantly better to the treatment with STS derivatives than brain cancer cells positive for PME-1 expression (Example 2). It is thus envisaged that the expression level of PME-1 in a sample obtained from a brain cancer patient can be used as a stratification criteria for identifying subjects who are likely to benefit from the treatment with STS derivatives and who are not.

As used herein, the term "STS derivative" refers to any compound structurally similar to STS, including, but not limited to, compounds of Formula (I) and any stereoisomers, racemates, salts, solvates or prodrugs thereof. The compounds of Formula (I) has the following general structure:

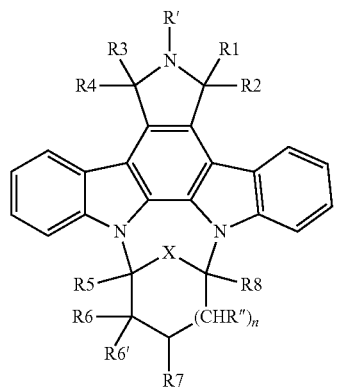

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and
n is 0 or 1.

The term "alkyl" referred to above include both linear and branched C1-6 alkyl groups, such as methyl, ethyl, propyl, butyl, pentyl, hexyl, and the like. In some embodiments, the alkyl group is a C1-3 alkyl group containing 1 to 3 carbon atoms.

As used herein, the term "alkoxy" refers to both linear and branched C1-6 alkoxy groups, such as methoxy, ethoxy, propoxy, and the like. In some embodiments, the alkoxy group is a C1-3 alkoxy group containing 1 to 3 carbon atoms.

As used herein, the term "hydroxyalkyl" refers to any of the above-mentioned C1-6 alkyl groups substituted by —OH.

As used herein, the term "alkoxycarbonyl" refers to any of the above-mentioned C1-6 alkoxy groups substituted by —COOH.

The term "amino" refers to —$NH_2$.

The term "monoalkylamino" includes any of the above-mentioned alkyl groups substituted with an amino group.

The term "dialkylamino" refers to any of the above-mentioned alkyl groups substituted with two amino groups.

As used herein, the term "stereoisomer" is a general term for all isomers of individual molecules that differ only in the orientation of their atoms in space. It includes enantiomers and isomers of compounds with more than one chiral center that are not mirror images of one another (diastereomers).

As used herein, the term "chiral center" or "asymmetric center" refers to a carbon atom to which four different groups are attached.

The term "enantiomer" refers to a molecule that is non-superimposeable on its mirror image and hence optically active, wherein the enantiomer rotates the plane of polarized light in one direction and its mirror image rotates the plane of polarized light in the opposite direction.

The term "racemate" refers to a mixture of equal parts of enantiomers and which is optically inactive.

Non-limiting examples of the STS derivatives of Formula (I) include the following:

Staurosporine (STS); chemical name [9S-(9α,10β,11β, 13α)]-2,3,10,11,12,13-Hexa-hydro-10-methoxy-9-methyl-11-(methylamino)-9,13-epoxy-1H,9H-diindolo[1,2,3-gh:3′,2′,1′-lm]pyrrolo[3,4-j][1,7]benzodiazonin-1-one; CAS number 62996-74-1:

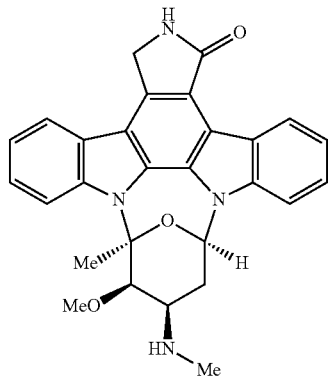 [SMILES: CN[C@@H]1C[C@H]2O[C@@](C)([C@@H]1OC)n1c3ccccc3c3c4c(c5c6ccccc6n2c5c31)C(=O)NC4]

PKC412, also known as Midostaurin, 4′-N-benzoyl staurosporine, or CGP 41251; chemical name [9S-(9α, 10β,11β, 13α)]-N-(2,3,10,11,12,13-Hexahydro-10-methoxy-9-methyl-1-oxo-9,13-epoxy-1H,9H-diindolo[1,2,3-gh:3′,2′,1′-lm]pyrrolo[3,4-j][1,7]benzodiazonin-11-yl)-N-methyl benzamide; CAS number 120685-11-2:

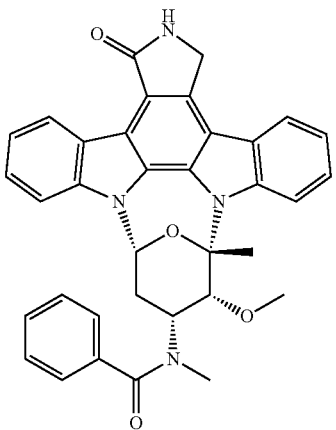 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4]

K252a, also known as SF 2370; chemical name 9S,10R, 12R)-2,3,9,10,11,12-Hexahydro-10-hydroxy-9-methyl-1-oxo-9,12-epoxy-1H-diindolo[1,2,3-fg:3′,2′,1′-kl]pyrrolo[3,4-i][1,6]benzodi-azocine-10-carboxylic acid methyl ester; CAS number 99533-80-9:

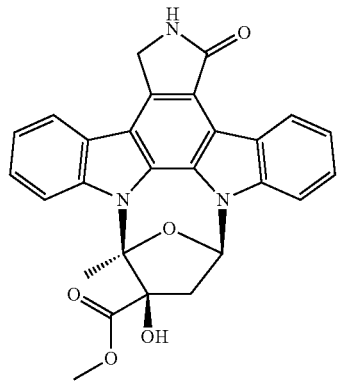 [SMILES: COC(=O)[C@@]1(O)C[C@H]2O[C@]1(C)n1c3ccccc3c3c4c(c5c6ccccc6n2c5c31)C(=O)NC4]

UCN-01, also known as 7-Hydroxy-staurosporine; chemical name (9S)-2,3,10,11,12,13-Hexahydro-3α-hydroxy-10α-methoxy-9-methyl-11α-methylamino-9β,13β-epoxy-1H,9H-diindolo[1,2,3-gh:3′,2′,1′-lm]pyrrolo[3,4-j][1,7]benzo diazonin-1-one; CAS number 112953-11-4:

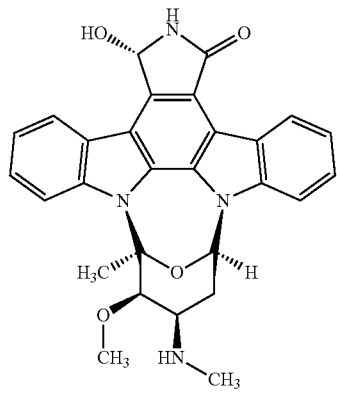

CEP-701, also known as Lestaurtinib; chemical name (9S,10S,12R)-2,3,9,10,11,12-Hexahydro-10-hydroxy-10-(hydroxymethyl)-9-methyl-9,12-epoxy-1H-diindolo[1,2,3-fg:3′,2′,1′-kl]pyrrolo[3,4-i][1,6]benzo di-azocin-1-one; CAS number 111358-88-4:

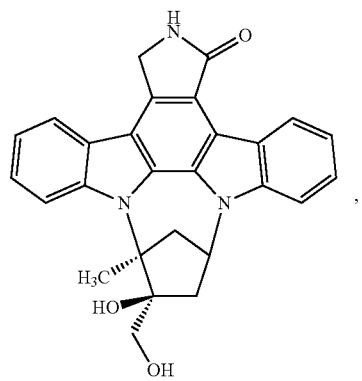 [SMILES: C[C@]12CC(C[C@]1(O)CO)n1c3ccccc3c3c4c(c5c6ccccc6n2c5c31)CNC4=O]

and

SB-218078; chemical name 9,10,11,12-Tetrahydro-9,12-epoxy-1H-diindolo[1,2,3-fg:3′,2′,1′-kl]pyrrolo[3,4-i][1,6]benzodi-azocine-1,3(2H)-dione; CAS number 135897-06-2:

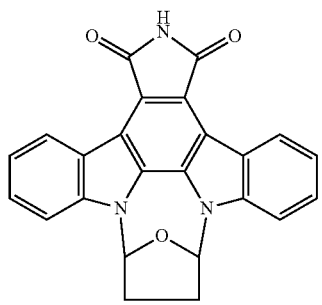 [SMILES: O=C1NC(=O)c2c1c1c3ccccc3n3c1c1c2c2ccccc2n1C1CCC3O1]

Herein, the expression "responsive to a treatment with a STS derivative" is equivalent to the expressions "sensitive to a STS derivative" and "susceptible to a treatment with a STS derivative", and means that a STS derivative may potentially have a therapeutic effect in a patient to whom the STS derivative is to be administered.

As used herein, the terms "treatment" and "therapeutic effect" refer not only to complete cure of a disease, but also to prevention, alleviation, and amelioration of a disease or symptoms related thereto. The terms "treatment" and "therapy" may be used interchangeably. Accordingly, the term "cancer therapy" includes, for instance, inhibition or stabilization of progression of cancer, tumour size, and/or number of metastases.

The therapeutic effect in a patient may be monitored by any method known to those with ordinary skill in the clinical art of treating cancer-related disorders. Such methods include, but are not limited to, tomography and detection of cancer markers.

Herein, the term "patient" refers to a human or animal subject in need of brain cancer therapy. Thus, the methods of the present invention are applicable to both human and veterinary applications.

Herein, the term "glioma" refers to primary brain tumors arising from glial cells and includes astrocytomas such as juvenile pilocytic astrocytoma, low grade astrocytoma, anaplastic astrocytoma, or glioblastoma, oligodendrogliomas, and ependymomas.

Surgical or biopsy specimens obtained from a glioma patient are typical sample types to be analyzed for the expression level of PME-1. According to some embodiments, the surgical or biopsy specimens obtained from a diseased brain tissue contains also adjacent healthy tissue in order to enable comparisons between the expression levels of PME-1 in said tissues. The expression level of PME-1 in a tissue sample may be determined by any suitable direct or indirect detection method known in the art. Such methods include, but are not limited to, immunohistochemistry using a PME-1 specific antibody. Such antibodies are available in the art and further anti-PME-1 antibodies may be developed as known to a skilled person. Detection of anti-PME-1 antibody binding may be performed through labels, such as fluorescent, luminescent, chromogenic, fotometric or radioactive labels. In addition, it is envisaged that the level of PME-1 protein expression may correlate with the level of PME-1 mRNA expression and could be determined e.g. by real-time PCR as known in the art.

By the terms "increased PME-1 expression" or "positive for PME-1 expression" it is meant significantly increased expression of PME-1 as compared to a related non-malignant tissue. In some embodiments, said significant increase is statistically significant. Statistical methods for assessing the significance of a difference in PME-1 expression levels are readily available in the art.

In some embodiments, the level of PME-1 expression is at least 1.5 fold, preferably at least 2 fold, as compared to a corresponding healthy tissue in order to be considered as increased.

Herein, the term "intact PME-1 expression" means that a diseased tissue does not express significantly higher levels of PME-1 than a corresponding healthy tissue.

In some embodiments, however, the expression of PME-1 might be slightly, i.e. by less than 1.5 fold, increased as compared to a corresponding non-malignant tissue and still be considered as intact.

According to an embodiment of the present invention, a patient whose glioma tissue is positive for PME-1 is likely to benefit less from a treatment with STS derivatives than a corresponding patient whose glioma tissue expresses intact levels of PME-1. Thus, therapy regimens other than treatment with STS derivatives, is recommended for patients positive for PME-1 expression.

On the other hand, it is envisaged that patients whose glioma tissue exhibits enhanced PME-1 expression may benefit from combined silencing of PME-1 expression, either at transcriptional or post-transcriptional level, and treatment with STS derivatives. Such a combination therapy may be administered simultaneously, sequentially, or separately. In some embodiments, said combination therapy may include surgery of the malignant tissue.

Means and methods for silencing PME-1 expression are readily available in the art, including, but not limited to, RNA interference (RNAi). Non-limiting examples of small RNAs suitable for mediating RNAi include small double-stranded RNAs (dsRNAs), small interfering RNAs (siRNAs), Dicer substrate siRNAs (DsiRNAs), artificial micro-RNA (miRNA) precursors, and short-hairpin RNAs (shRNAs). PME-1 specific sRNA molecules have been disclosed e.g. in US patent publication US 2009/182134 (SEQ ID NOs: 5 to 34), while Finnish patent application FI 20115640 discloses PME-1 specific siRNAs and shRNAs (SEQ ID NOs: 35 to 40). Further dsRNA molecules may be designed by using commercial and non-commercial algorithms as known to a skilled person.

Examples of other ways of silencing PME-1 expression include use of single-stranded antisense oligonucleotides (either RNA or DNA) and ribozyme technology, as well known in the art.

Any of the molecules to be used for silencing PME-1 gene expression may be modified according to standard methods known in the art.

According to a further embodiment of the present invention, patients whose glioma tissue expresses intact levels of PME-1 are likely to benefit from monotherapy with STS derivatives. As used herein, the term "monotherapy" refers to a therapy with at least one STS derivative without silencing of PME-1 expression. If desired, said STS therapy may be combined with a surgery and/or with any synergizing or additive chemotherapy.

It will be obvious to a person skilled in the art that, as the technology advances, the inventive concept can be implemented in various ways. The invention and its embodiments are not limited to the examples described above but may vary within the scope of the claims.

Examples

Materials and Methods

Eukaryotic Cell Culture and Small Interfering RNA (siRNA) Transfections:

For this study, we used T98G, U118MG, U251MG and U87MG human glioblastoma cell lines. T98G and U251MG cells were cultured in Eagle's MEM, U118MG in DMEM (Sigma-Aldrich) and U87MG in DMEM/F-12 (Gibco Products, Invitrogen) media supplemented with 10% heat-inactivated FCS and penicillin (100 units/mL)-streptomycin (100 Ag/mL) in a humidified atmosphere of 5% $CO_2$ at 37° C. Small interfering RNA (siRNA) transfections were performed with Lipofectamine RNAiMAX reagent (Invitrogen) according to the manufacturer's instructions. Transfections were performed using forward transfection protocol in all the experiments except for CellTiter-glo and Caspase-glo assay, where reverse transfections were performed in 96-well plates. Following siRNA sequences were used: scrambled (5'-GUA ACA AUG AGA GCA CGG C-3'; SEQ ID NO:4), PME-1 (5'-GGA AGU GAG UCU AUA AGC A-3'; SEQ ID NO:1), PME-1 (5'-UCA UAG AGG AAG AAG AAG A-3'; SEQ ID NO:2) or PME-1 (5'-AGG UCA AGA AUC CUG AAG A-3'; SEQ ID NO:3).

Chemical Inhibitors and Drugs:

A small inhibitor screening set containing H-7, H-8, H-89, Chelerythrine chloride (Chl Cl), Sunitinib, Tandutinib, Lapatinib, Vandetanib, PKC412 and K252a was purchased from Biaffin GmbH & Co KG. Topotecan Hydrochloride was purchased from Selleck Chemicals. UO126, LY 294002, RO-31-8220, GÖ 6976 and SB 218078 were purchased from Calbiochem. Staurosporine (STS), CEP-701, UCN-01 were obtained from Sigma-Aldrich; Temozolomide (TMZ), Arcyriaflavin-A and K252c from Tocris Bioscience; Rebeccamycin from Enzo Life Sciences and Enzastaurin from LC laboratories. Pan-caspase inhibitor Z-VAD-FMK, PP2A inhibitor Okadaic acid, and activators Sodium selenate and Xylulose-5-phosphate were obtained from Sigma-Aldrich. Another PP2A activator FTY720 was purchased from Cayman chemicals. Human recombinant Fc-FasL fusion protein and human recombinant isoleucine-zipper TRAIL (TRAIL) were a gift from Professor John Eriksson (Åbo Akademi University). All the chemicals were reconstituted as recommended by the supplier in either water or DMSO.

Western Blotting and Antibodies:

Cultured and treated cells were lysed in 2×SDS sample buffer/Laemmli Buffer, boiled and resolved by SDS-PAGE using 10% acrylamide gels. Proteins were transferred to PVDF membranes. Membranes were blocked and incubated with required dilution of primary and 1:5000 dilution of secondary antibody in 5% Milk-PBS-Tween20 for required duration of time and developed by enhanced chemiluminescence (ECL). Anti-PME-1 (clone H-226) and anti-CIP2A (clone 2G10-3B5) antibodies (1:1000 dilution) were purchased from Santa Cruz Biotechnology. Anti-actin (clone AC-40) antibody (1:10,000 dilution) was purchased from Sigma-Aldrich. Densitometric analysis of western blots was performed using MCID image analyzer software.

Cell Viability Assay:

Cell viability was determined by CellTiter-glo (CTG) assay which measures the cellular ATP levels as an indicator of metabolically active and viable cells. CTG reagent kit was purchased from Promega Corp. and assays were performed according to their recommendations. Assays were performed in white polystyrene 96-well plates (Nunc, Thermo Fisher Scientific Inc.) and luminescence was measured with Perkin Elmer Victor2 Plate Reader.

Analysis of Caspase-3 and -7 Activity:

Caspase-3 and -7 activity was measured by luminescence based method, which utilize a substrate containing Caspase-3 and -7 target peptide DEVD, named Caspase-Glo 3/7 Assay (Promega Corp.). Assays were performed in white polystyrene 96-well plates (Nunc, Thermo Fisher Scientific Inc.) according to manufacturer's instructions and luminescence was measured with Perkin Elmer Victor2 Plate Reader.

Apoptosis Assay by Sub-G0/G1 Fraction Estimation:

The percentage of the sub-G0/G1 fraction containing fragmented nuclei stained with Propidium iodide (PI) was taken as a measure of apoptotic cells. $3.5$-$4 \times 10^4$ cells were plated in 24-well plates, transfected with siRNA for 48 hrs, and then treated with indicated concentration of test compounds in fresh media. After 24 hrs of treatment, both floating and adherent cells were harvested by centrifugation. Cell pellets were resuspended in 400 µl of hypotonic PI buffer, containing 40 mM Tri-sodium citrate (Merck), 0.3% Triton X-100 (Sigma-Aldrich) and 50 µg/ml Propidium iodide (Sigma-Aldrich) in PBS, and incubated at room temperature for 10 minutes in dark. The flow cytometric analysis of PI stained nuclei was performed and the recorded data was analyzed using a FACScan flow cytometer and software (Becton Dickinson) respectively.

In experiments using pan-caspase inhibitor, cells were kept in growth media containing 30 µM Z-VAD-FMK starting from 18 hrs after transfection till the PI staining.

Colony Formation Assay:

Cells plated in very low density ($4$-$6 \times 10^3$) in 6-well plates were allowed to grow for about 7 days until they form small colonies. These cells were then transfected with Scrambled or PME-1 siRNA using Lipofectamine RNAiMAX reagent (Invitrogen) according to the manufacturer's instructions. After 48 hrs, treatments were given with indicated concentration of chemical drugs for another 48 hrs. Cell colonies were washed with PBS, fixed with 3.7% formaldehyde and stained with 0.2% crystal violet solution (made in 10% ethanol) for 15 minutes at room temperature each. Excess stain was removed by repeated washings with PBS. Plates were dried and pictures were taken with Olympus SP-600UZ camera or Epson perfection V700 scanner and analysed with ImageJ.

Statistical Analysis:

The significance level of differences between the mean values of two groups of data was evaluated using the unpaired Student's t-test assuming equal variances among the sample means. All p-values were two-tailed. Parameters with probability value $p<0.05$ was depicted as statistically significant and $p<0.001$ as highly significant difference.

Results

In order to study the role of PME-1 in cancer cell survival and sensitivity to different chemical drugs, human glioblastoma T98G cells were transiently transfected with PME-1 siRNA for 72 hs to effectively reduce PME-1 protein levels (FIG. 1A). The T98G cells containing normal or reduced levels of PME-1 (cells transfected with Scrambled siRNA depicted in SEQ ID NO:4 or PME-1 siRNA depicted in SEQ ID NO:1, respectively) were treated with different chemical drugs including broadly specific inhibitors of serine-threonine protein kinases (H7, H8, H89, Chelerythrine chloride, UO126, LY 294002 and Staurosporine), inhibitors of tyrosine kinases (Sunitinib, Tandutinib, Lapatinib and Vandetanib), DNA topoisomerase I inhibitor (Topotecan) and a DNA methylating drug, Temozolomide (TMZ), which is currently used for the treatment of glioblastoma multiforme (GBM).

Figure 1B:
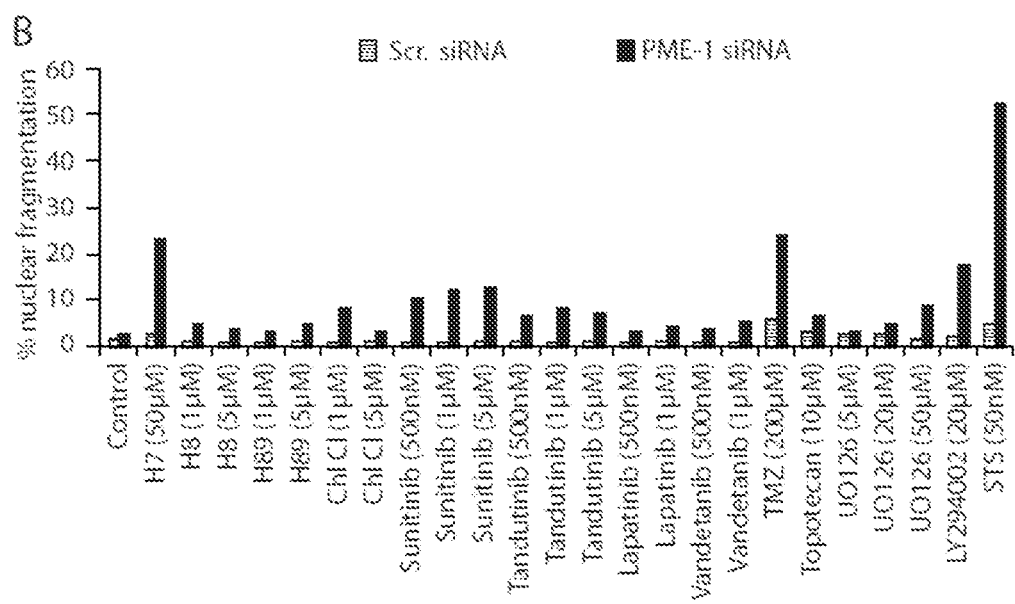
FIG. 1B displays the amount of apoptotic nuclear fragmentation in T98G glioblastoma cells transfected with either scrambled or PME-1 specific dsRNA for 48 hours, and then treated with indicated concentration of different drugs/chemical inhibitors for another 24 hours. Abbreviations: Chl Cl—chelerythrine chloride, TMZ—temozolomide, STS—staurosporine.

The T98G cells transfected with siRNA for 48 hrs were given drug treatments for 24 hrs and were subsequently lysed, and their nuclei were stained using hypotonic propidium iodide buffer. The lysates were analysed for changes in the sub-G0/G1 fraction of fragmented nuclei by flow cytometry (FACS) (FIG. 1B). Condensation and fragmentation of nucleus is a key biochemical feature of apoptosis and sub-G0/G1 analysis has been widely used for detection of apoptosis (FEBS Lett., 1986, 194(2):347-50; Cytometry, 1991, 12(4):323-329; Nature Protocols, 2006, 1:1458-1461).

Figure 1C:
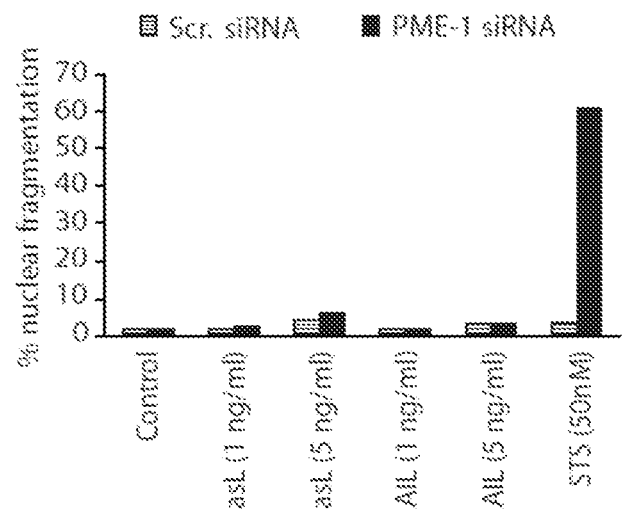
FIG. 1C shows the amount of apoptotic nuclear fragmentation in T98G glioblastoma cells transfected with either scrambled or PME-1 specific dsRNA for 48 hours, and then treated with indicated concentrations of staurosporine (STS) or cell death inducing ligands, recombinant FasL or TRAIL, for another 24 hours.

As illustrated in FIG. 1B, T98G cells expressing intact levels of PME-1 did not respond well to the treatment with drugs other than TMZ and STS. However, depletion of PME-1 increased the cells' sensitivity to STS outstandingly, as judged by the very high level of nuclear fragmentation induced. Depletion of PME-1 increased the apoptosis-inducing effect of all the chemicals tested to some extent but only the effect of H7, Sunitinib, LY 294002, and TMZ was considered as moderate. In other words, the synergistic effect of PME-1 depletion was found to be specific to STS because treatment of cells with most of the chemical compounds (FIG. 1B) or with cell death inducing ligands, FasL (recombinant Fc-FasL fusion protein) and TRAIL (FIG. 1C) did not show the same trend.

Figure 1D:
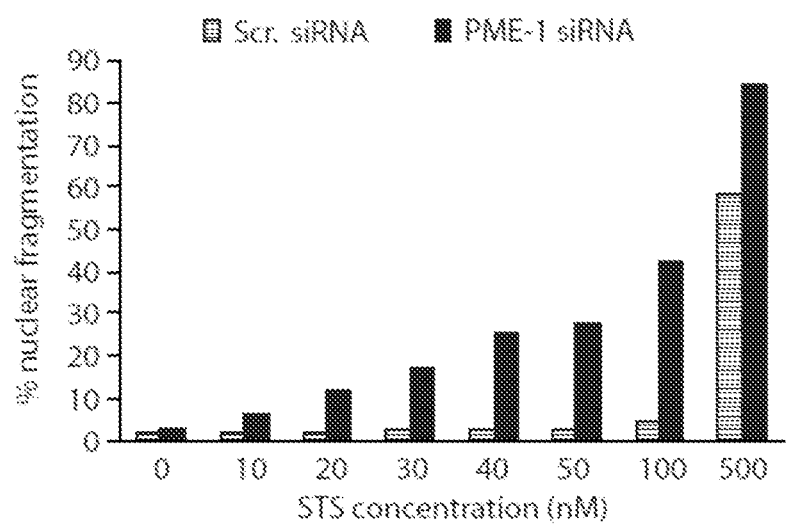
FIG. 1D shows the dose dependent increase in the apoptosis of PME-1 dsRNA transfected T98G cells with increasing concentration of staurosporine, as compared to scrambled dsRNA transfected cells.

Moreover, STS was found to induce apoptosis in a dose dependent manner in PME-1 depleted cells at concentrations that did not induce cell death in scrambled siRNA transfected cells (FIG. 1D). However, at concentrations higher than 50 nM, STS alone started inducing cell death even in control (Scrambled siRNA transfected) T98G cells.

Figure 1E:
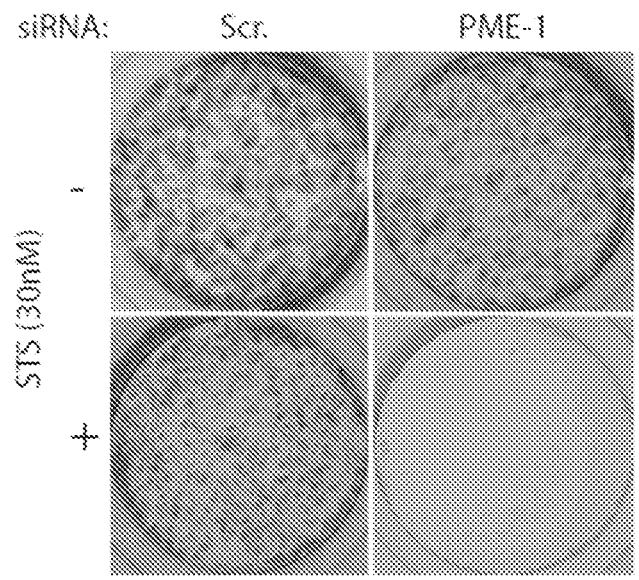
FIGS. 1E and 1F represent the colonogenic potential of T98G and U118MG glioblastoma cells respectively, after transfection of scrambled or PME-1 dsRNA and treatment with indicated concentration of staurosporine for 2 days.
Figure 1F:
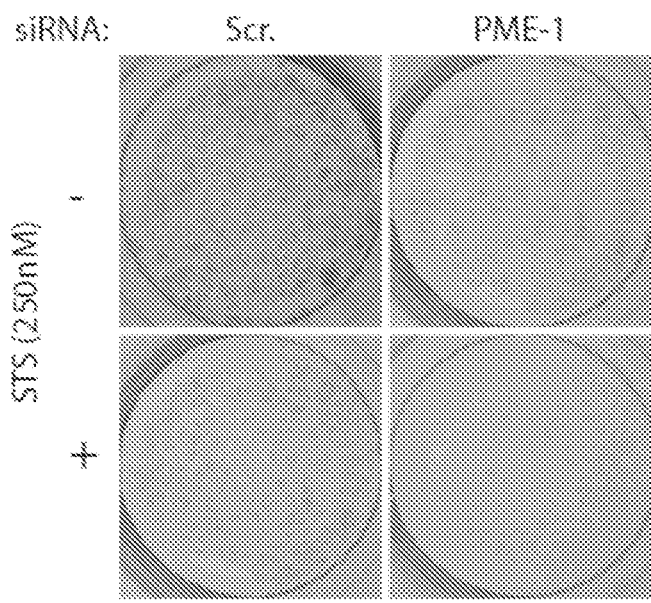

Next, the effect of PME-1 expression on the sensitivity of glioblastoma cells to STS was tested by colony formation assay in T98G glioblastoma cells and another glioblastoma cell line U118MG. For this experiment, these cells were grown in 6-well plates until the formation of small colonies which were then transfected with Scrambled or PME-1 siRNA for 48 hrs followed by treatment with STS at the indicated concentrations for another 48 hrs. Colonies were fixed with formaldehyde, stained with crystal violet and pictures were analyzed with Image J. Cells expressing intact levels of PME-1 did not respond well to STS treatment, whereas PME-1 depletion sensitized the cells and resulted in almost complete loss of colonies (FIGS. 1E and 1F). Similar results were obtained with both glioblastoma cell lines.

Figure 2A:
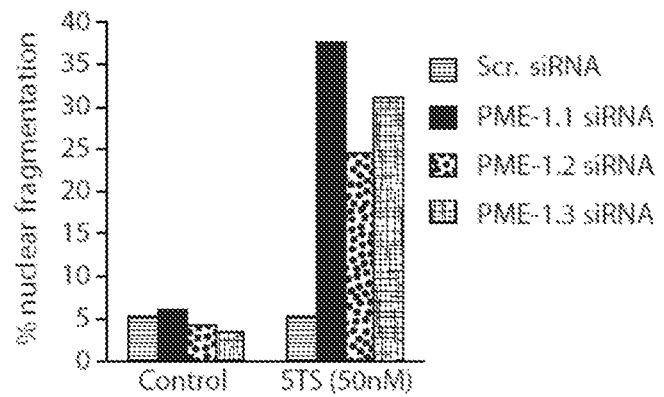
FIG. 2A represents the induction of apoptotic nuclear fragmentation by three different PME-1 dsRNAs, PME-1.1 (SEQ ID NO:1), PME-1.2 (SEQ ID NO: 2) and PME-1.3 (SEQ ID NO: 3), in combination with staurosporine treatment.
Figure 2B:
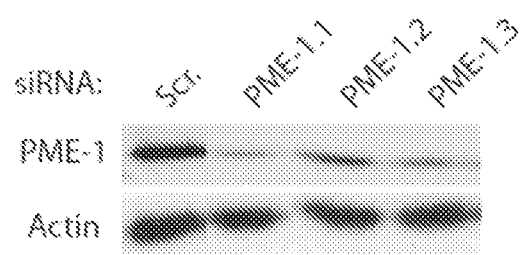
FIG. 2B a western blot demonstrating PME-1 silencing activity of a scrambled dsRNA (Scr.) and three different PME-1 specific dsRNAs (PME-1.1, i.e. SEQ ID NO: 1, PME-1.2, i.e. SEQ ID NO: 2, and PME-1.3, i.e. SEQ ID NO: 3) in T98G cells.
Figure 2C:
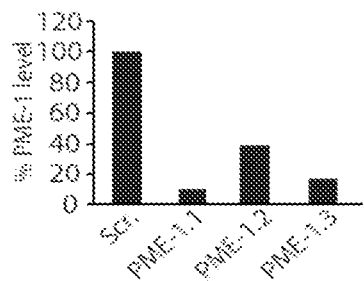
FIG. 2C is the densitometric analysis of above mentioned western blot image showing residual PME-1 levels in T98G cells transfected with PME-1 specific dsRNAs (PME-1.1, i.e. SEQ ID NO: 1, PME-1.2, i.e. SEQ ID NO: 2, and PME-1.3, i.e. SEQ ID NO: 3) as compared to scrambled siRNA transfected cells.
Figure 2D:
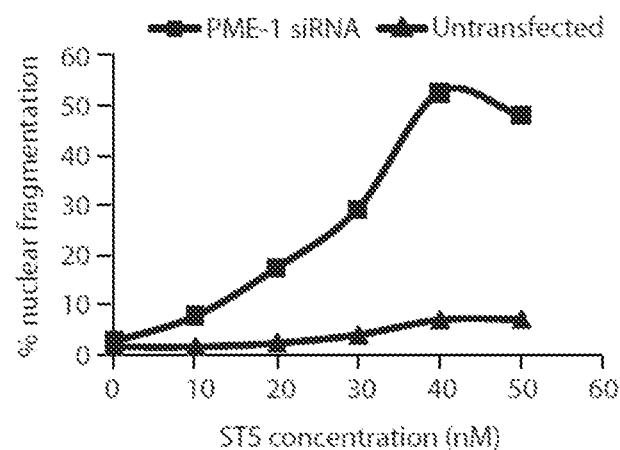
FIG. 2D shows the dose dependent increase in the apoptosis of PME-1 dsRNA transfected T98G cells with increasing concentration of staurosporine as compared to untransfected cells.

To exclude the possibility of sequence-specific off-target effect of the PME-1 siRNA used (SEQ ID NO: 1) in the above experiments, three different PME-1 specific siRNA sequences (SEQ ID NOs: 1 to 3) were transfected to T98G cells and apoptotic nuclear fragmentation was analyzed following STS treatment (FIG. 2A). Effectiveness of these PME-1 siRNAs was measured by western blotting (FIG. 2B), and band intensities were quantified and normalized with respect to beta-actin (FIG. 2C). All PME-1 siRNA sequences were capable of sensitizing glioblastoma T98G cells to STS mediated apoptosis. To eliminate any possible background effects caused by transfection of Scrambled siRNA, untransfected T98G cells were treated with increasing concentration of STS and the apoptotic nuclear fragmentation in these cells was compared with the cells receiving PME-1 siRNA and same concentration of STS (FIG. 2D). We observed limited amount of cell death with STS alone at concentrations higher than 30 nM. On the other hand, cells downregulated for PME-1 were highly sensitive to STS induced cell death even at lowest concentrations used in this experiment.

Figure 3A:
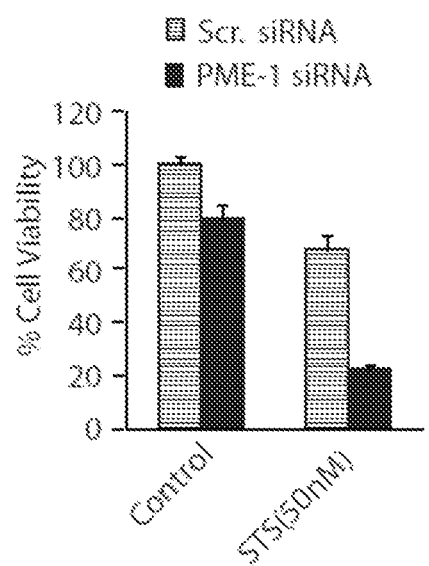
FIG. 3A shows the effect of PME-1 dsRNA transfection and staurosporine treatment on the viability of T98G cells.

To study the features of cell killing induced by STS in PME-1 depleted cells we first analyzed the effect of this dual combination of PME-1 siRNA and STS treatment on viability of glioblastoma T98G cells by Cell-titer-glo (CTG) assay (FIG. 3A). The results strongly correlate with the sub-G0/G1 analysis as PME-1 depletion reduced cell viability by small fraction but when the same cells also received the STS treatment there was a drastic decrease in the cell viability.

Figure 3B:
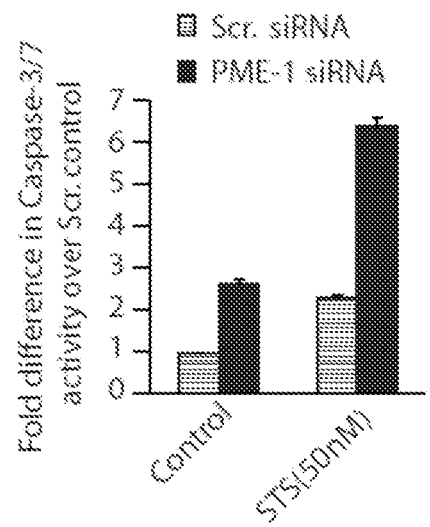
FIG. 3B shows the effect of PME-1 dsRNA transfection and staurosporine treatment on the levels of active caspase-3 and -7 in T98G cells.
Figure 3C:
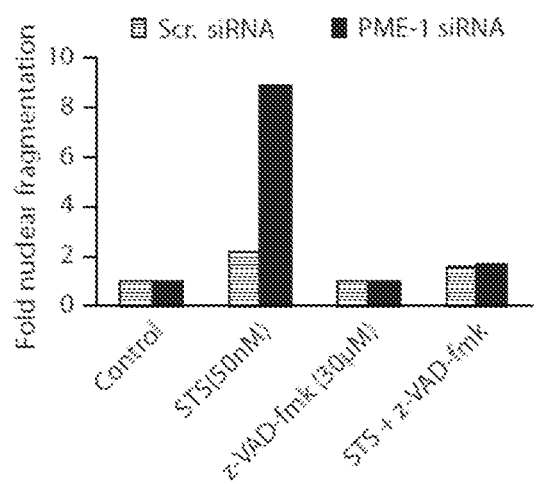
FIG. 3C shows the effect of pan-caspase inhibitor, Z-VAD-FMK treatment on PME-1 dsRNA and staurosporine mediated apoptosis, measured as the amount of nuclear fragmentation.

Another biochemical feature of apoptosis is activation of effector cysteine-aspartic proteases Caspase-3 and 7. PME-1 depletion alone was found to increase the activity of Caspase-3/7 by more than 2 fold which in combination with STS treatment rises above 6 fold (FIG. 3B) suggesting Caspases are involved in apoptosis induction. To further verify the role of Caspase induction, cells receiving PME-1 siRNA and STS treatment were treated with pan-caspase inhibitor, z-VAD-fmk, throughout the experiment and apoptosis was analyzed by nuclear fragmentation assay (FIG. 3C). We found a complete reversal of STS mediated apoptosis in PME-1 depleted cells by inhibition of Caspase activity, suggesting that this apoptosis is completely dependent on induction of Caspases.

Figure 4A:
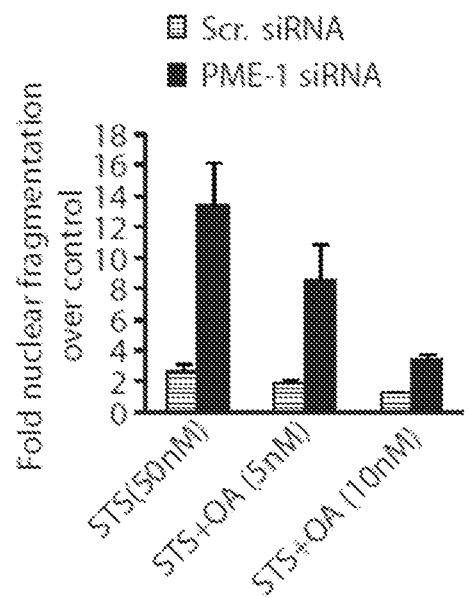
FIG. 4A shows the effect of pre-treatment of T98G cells with PP2A inhibitor, okadaic acid, on PME-1 dsRNA and staurosporine mediated apoptosis, measured as amount of nuclear fragmentation.
Figure 4B:
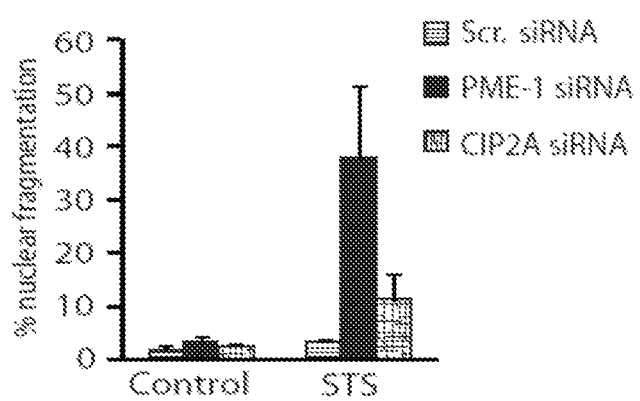
FIG. 4B shows a comparison between the apoptosis inducing potential of PME-1 specific or CIP2A specific dsRNA upon staurosporine treatment in comparison to scrambled dsRNA transfected cells.
Figure 4C:
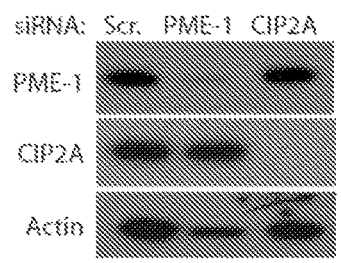
FIG. 4C is a western blot image demonstrating the PME-1 and CIP2A silencing activity of a scrambled dsRNA (Scr.), PME-1 specific dsRNA (PME-1) and CIP2A specific dsRNA (CIP2A) in human glioblastoma T98G cells.

Next, our focus was to investigate the possible mechanism behind PME-1 mediated resistance of glioblastoma cells to STS induced apoptosis. Since the only established direct target of PME-1 is PP2A, we used a chemical inhibitor of PP2A, okadaic acid (OA) speculating that it should reverse the effect of PME-1 inhibition and hence promote the cell survival. Indeed, pre-treatment of glioblastoma T98G cells with OA for 24 hrs prior STS treatment was sufficient to rescue cells from PME-1 siRNA and STS mediated apoptosis in a dose dependent manner (FIG. 4A). This led us to look further whether these PP2A-mediated apoptosis effects are specific to PME-1 or shared with other PP2A inhibitory/regulatory proteins, we compared CIP2A and PME-1 depletion for their ability to sensitize glioblastoma cells to apoptosis in response to STS treatment. We found that CIP2A down-regulation increased apoptosis to very small extent so that it cannot be considered as synergistic effect as mediated by PME-1 depleted cells (FIG. 4B), supporting the idea that these effects are specific to PME-1 down-regulation. Effective downregulation of CIP2A and PME-1 by their respective siRNAs was verified by western blotting (FIG. 4C).

All the above results demonstrate that glioblastoma cells positive for PME-1 do not respond well to treatment with STS. On the other hand, glioblastoma cells with intact PME-1 expression are sensitive to STS mediated apoptosis.

Figure 5A:
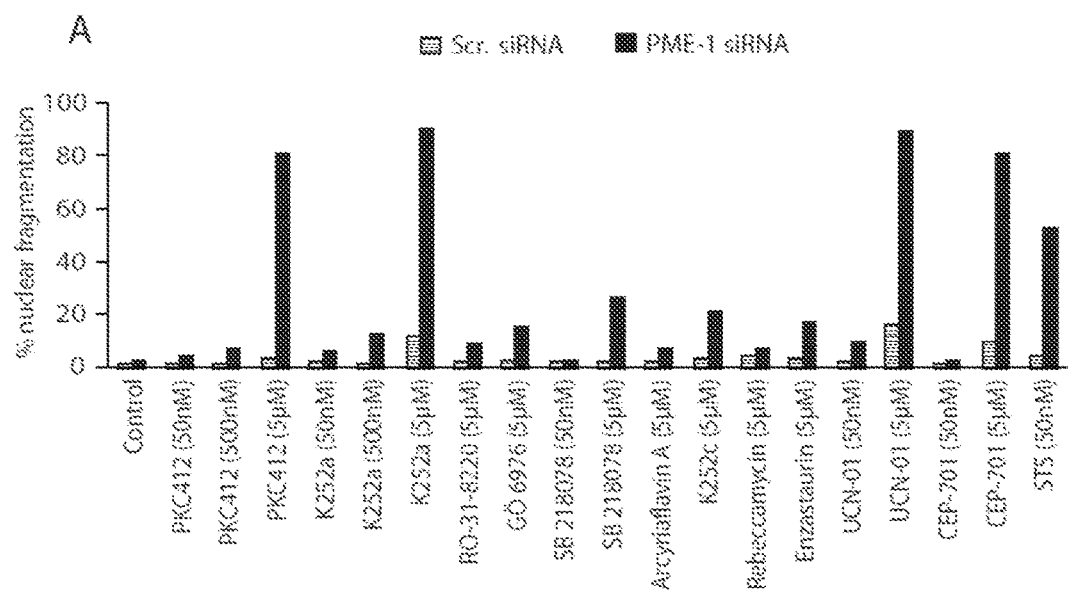
FIG. 5A shows the amount of apoptotic nuclear fragmentation in T98G glioblastoma cells after transfection with either scrambled or PME-1 specific dsRNA for 48 hours and treatment with indicated concentration of different staurosporine derivatives/derivatives for another 24 hours.

Since STS has been documented in the literature as a broadly specific inhibitor of kinases, it is not considered to be a clinically relevant therapeutic agent. But, some STS derivatives are known which are far more specific and have fewer side effects and are currently in clinical trials for treatment of different diseases. So, we replaced STS with its derivatives, PKC412, K252a, RO-31-8220, GÖ 6976, SB 218078, Arcyriaflavin A, K252c, Rebeccamycin, Enzastaurin, UCN-01 or CEP-701 in our experimental setup at different concentrations (FIG. 5A). To our surprise, we found PKC-412, K252a, UCN-01 and CEP-701 being capable of inducing apoptosis in PME-1 depleted glioblastoma cells at levels even higher than STS itself. SB 218078 induced moderate levels of apoptosis at higher concentration. Glioblastoma cells expressing intact levels of PME-1 did not respond to any of the STS derivatives tested.

Figure 5B:
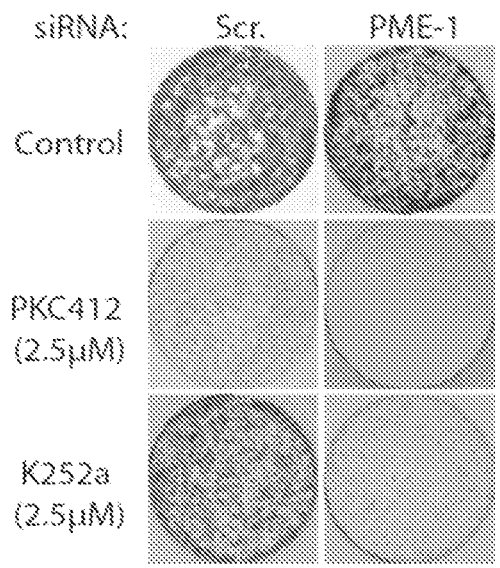
Figure 5C:
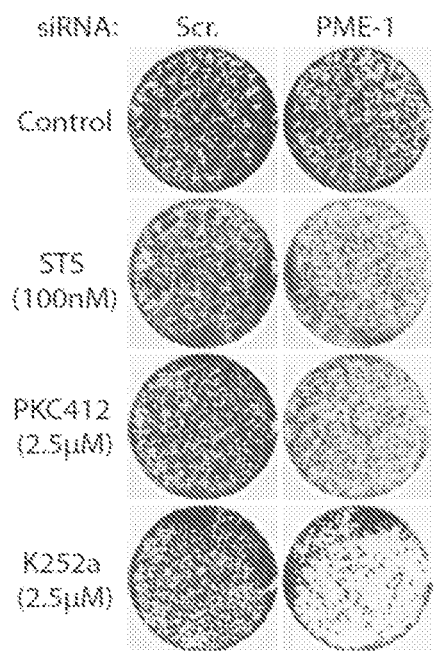
Figure 5D:
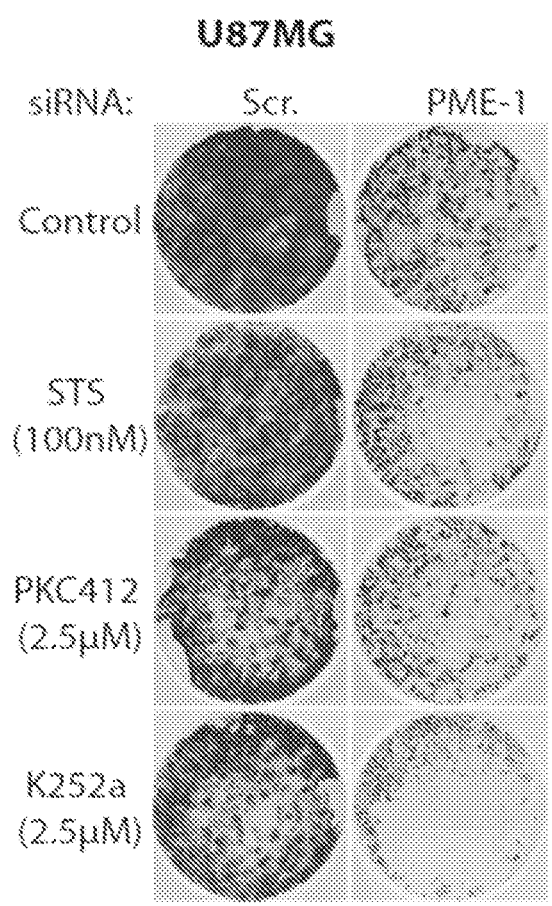

Colony formation assay in T98G cells using two active drugs, PKC412 and K252a also corroborate the above finding (FIG. 5B). In order to avoid the cell line specific effects, we also studied the efficacy of apoptosis sensitizing drugs, STS, PKC412 and K252a, in other PME-1 depleted glioblastoma cell lines U251MG and U87MG. In all studied cell lines, PME-1 depletion enhanced the cell killing activity of STS, PKC412, and K252a, although there were cell type dependent differences in the efficacy of the treatment combinations (FIGS. 5C and 5D).

The invention claimed is:

1. A method of selecting a brain cancer therapy for a patient in need thereof and treating a patient susceptible to brain cancer, wherein the method comprises:
   a) assessing the expression level of PME-1 in a sample obtained from said patient;
   b) selecting a brain cancer therapy for a patient in need thereof based on the expression level of PME-1 in the sample obtained in step a) compared to a corresponding non-malignant tissue,
   wherein increased PME-1 expression indicates that said patient is not susceptible to monotherapy with a staurosporine (STS) derivative, but said patient is susceptible to a combination therapy with the STS derivative and a PME-1 silencing agent,
   wherein intact PME-1 expression indicates that said patient is susceptible to glioma therapy with a STS derivative; and
   c) administering a brain cancer monotherapy or combination therapy selected in step b) to said patient,
   wherein said monotherapy in step c) is at least one STS derivative without a PME-1 silencing agent,
   wherein said combination therapy in step c) is simultaneously, sequentially, or separately of at least one STS derivative and the PME-1 silencing agent to said patient susceptible to brain cancer therapy,
   wherein said PME-1 silencing agent is a siRNA, and
   wherein said siRNA is at least one selected from the group consisting of SEQ ID NO: 1, SEQ ID NO: 2, and SEQ ID NO: 3,
   wherein said STS derivative has the general Formula (I):

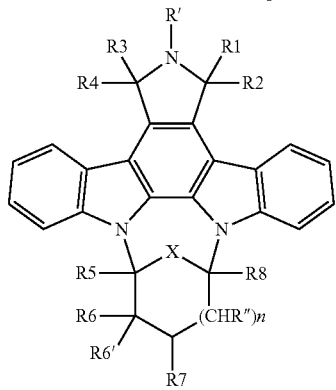

wherein
R' is H or alkyl,
R1 and R2 are H or together form oxo;
R3 and R4 are independently H, OH or together form oxo;
R5, R6, R6', and R8 are independently selected from the group consisting of H, alkyl, alkoxy, hydroxy, hydroxylakyl, alkoxycarbonyl, or mono- and dialkylamino;
R7 is selected from the group consisting of H, alkyl, alkoxy, hydroxy, hydroxylakyl, alkoxycarbonyl, or mono- and dialkylamino and N-methyl benzamide;
X is $CH_2$ or O; and
n is 0 or 1.

2. The method according to claim 1, wherein said STS derivative is selected from the group consisting of the following structures:

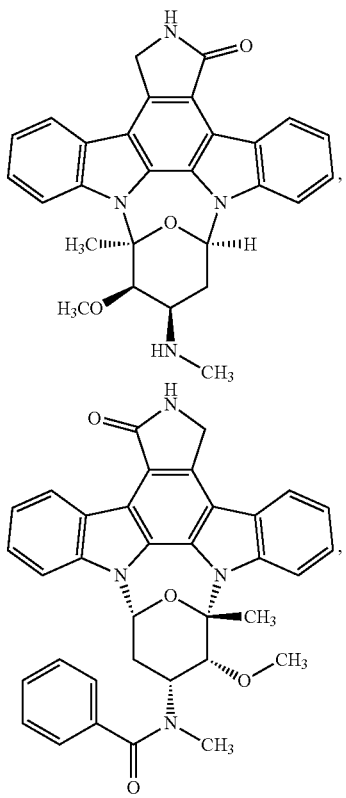

-continued

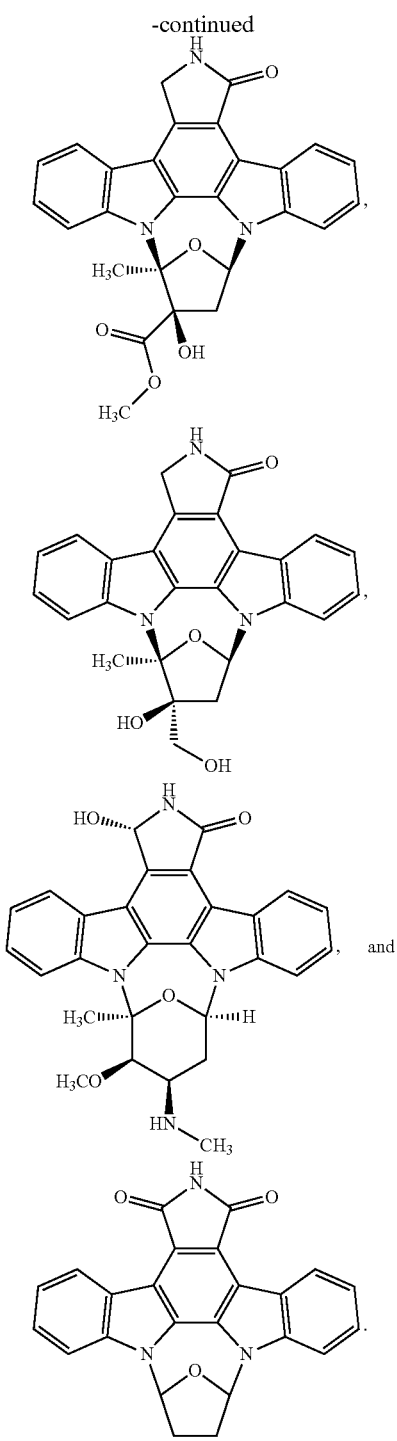

3. The method according to claim 1, wherein said combination therapy further includes surgery of a malignant tissue.

4. The method according to claim 1, wherein the sample is a glioma tissue.

5. The method of claim 1, which comprises administering a monotherapy of at least one STS derivative to said patient susceptible to brain cancer therapy.

6. The method according to claim 5, wherein said monotherapy further includes surgery of a malignant tissue and/or with any or additive chemotherapy.

7. The method according to claim 5, wherein the sample is a glioma tissue.

8. The method according to claim 5, wherein said STS derivative is selected from the group consisting of the following structures:

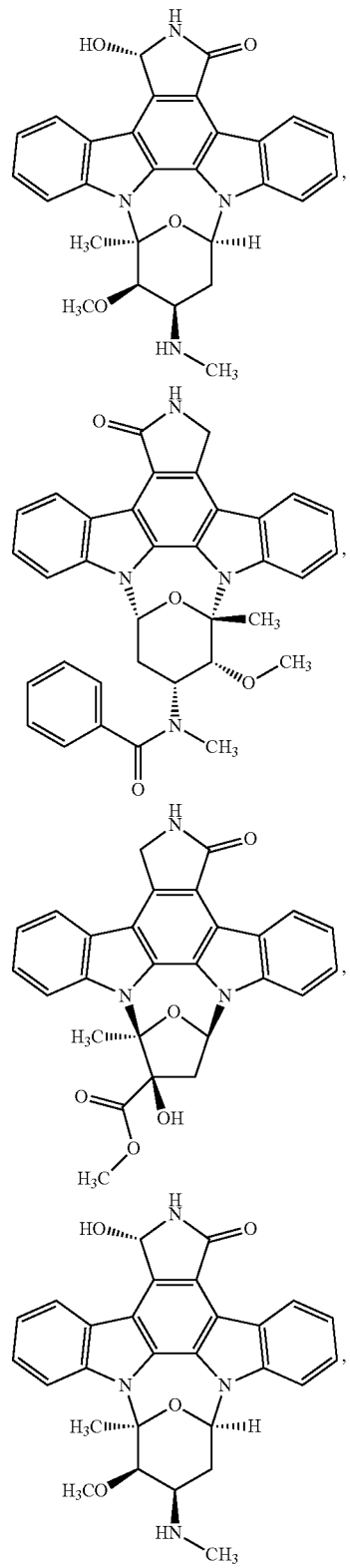

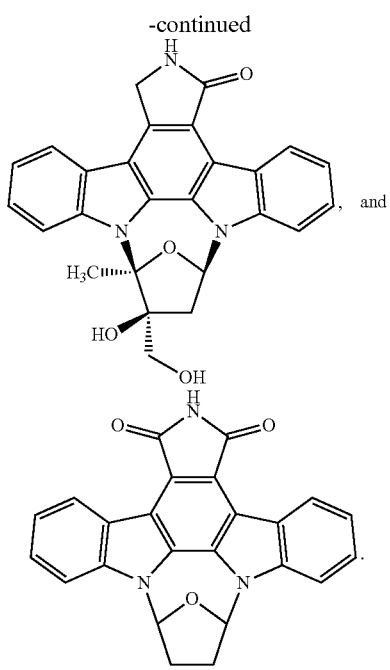, and
9. The method according claim 8, wherein said STS derivative is the following structure:
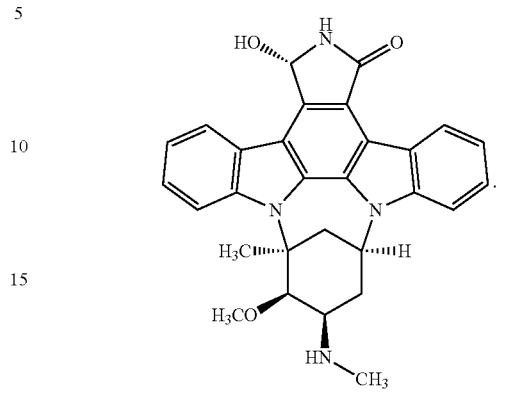
10. The method according claim 1, wherein said siRNA is at least one selected from the group consisting of SEQ ID NO: 2 and SEQ ID NO: 3.
* * * * *

```
                            SEQUENCE LISTING

<160> NUMBER OF SEQ ID NOS: 40

<210> SEQ ID NO 1
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 1
ggaagugagu cuauaagca                                                    19

<210> SEQ ID NO 2
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 2
ucauagagga agaagaaga                                                    19

<210> SEQ ID NO 3
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 3
aggucaagaa uccugaaga                                                    19

<210> SEQ ID NO 4
<211> LENGTH: 19
<212> TYPE: RNA
<213> ORGANISM: Artificial Sequence
<220> FEATURE:
<223> OTHER INFORMATION: Scrambled siRNA

<400> SEQUENCE: 4
guaacaauga gagcacggc                                                    19

<210> SEQ ID NO 5
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 5
ggaaggaauc auagaggaa                                                    19

<210> SEQ ID NO 6
<211> LENGTH: 19
<212> TYPE: RNA
<213> ORGANISM: Artificial Sequence
<220> FEATURE:
<223> OTHER INFORMATION: PME-1 siRNA
```

```
<400> SEQUENCE: 6
ggccaaagcc uauggaauu                                                    19

<210> SEQ ID NO 7
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 7
auguagaagu agagaauga                                                    19

<210> SEQ ID NO 8
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 8
ggucaagaau ccugaagau                                                    19

<210> SEQ ID NO 9
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 9
cugcagaaac aauggcaaa                                                    19

<210> SEQ ID NO 10
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 10
gcgaagucau ggugaaaca                                                    19

<210> SEQ ID NO 11
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 11
cauggaagau guagaagua                                                    19

<210> SEQ ID NO 12
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 12
agaagaagaa gaugaggaa                                                    19
```

-continued

```
<210> SEQ ID NO 13
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 13
gcgaaugggc ccuggaaga                                                19

<210> SEQ ID NO 14
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 14
aggaagaaga agaagauga                                                19

<210> SEQ ID NO 15
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 15
agauguagaa guagagaau                                                19

<210> SEQ ID NO 16
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 16
ucuauaagca agaggaaaa                                                19

<210> SEQ ID NO 17
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 17
aaucauagag gaagaagaa                                                19

<210> SEQ ID NO 18
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 18
ggguaaagcc uccagauuu                                                19

<210> SEQ ID NO 19
<211> LENGTH: 19
<212> TYPE: RNA
<213> ORGANISM: Artificial Sequence
<220> FEATURE:
<223> OTHER INFORMATION: PME-1 siRNA
```

```
<400> SEQUENCE: 19
caaacagugu gaaggaauu                                                 19

<210> SEQ ID NO 20
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 20
ggagaauuga acuggcaaa                                                 19

<210> SEQ ID NO 21
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 21
ucauagagga agaagaaga                                                 19

<210> SEQ ID NO 22
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 22
gcuauugaau ggaguguga                                                 19

<210> SEQ ID NO 23
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 23
cuuaauagca ugcagaauu                                                 19

<210> SEQ ID NO 24
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 24
gaaugaaacu ggcaaggau                                                 19

<210> SEQ ID NO 25
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 25
aagaugacau ggagaccaa                                                 19
```

```
<210> SEQ ID NO 26
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 26
uggaagaugu agaaguaga                                                  19

<210> SEQ ID NO 27
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 27
aaggaaucau agaggaaga                                                  19

<210> SEQ ID NO 28
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 28
aaucuauagu ggaaggaau                                                  19

<210> SEQ ID NO 29
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 29
ccaagaaaga ccauccaua                                                  19

<210> SEQ ID NO 30
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 30
caugauugau guuguagaa                                                  19

<210> SEQ ID NO 31
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 31
guggauagca ucacaagaa                                                  19

<210> SEQ ID NO 32
<211> LENGTH: 19
<212> TYPE: RNA
<213> ORGANISM: Artificial Sequence
<220> FEATURE:
<223> OTHER INFORMATION: PME-1 siRNA
```

```
<400> SEQUENCE: 32
cauagaggaa gaagaagaa                                               19

<210> SEQ ID NO 33
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 33
gaacaaaggu caagaaucc                                               19

<210> SEQ ID NO 34
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 34
gaaucauaga ggaagaaga                                               19

<210> SEQ ID NO 35
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 35
acagugugaa ggaauuaca                                               19

<210> SEQ ID NO 36
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 36
ucuauagugg aaggaauca                                               19

<210> SEQ ID NO 37
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 37
gguacagcua uggaugcac                                               19

<210> SEQ ID NO 38
<211> LENGTH: 21
<212> TYPE: DNA
<213> ORGANISM: Artificial Sequence
<220> FEATURE:
<223> OTHER INFORMATION: PME-1 shRNA

<400> SEQUENCE: 38
ctggtgttga tagattggat a                                            21
```

```
<210> SEQ ID NO 39
<211> LENGTH: 21
<212> TYPE: DNA
<213> ORGANISM: Artificial Sequence
<220> FEATURE:
<223> OTHER INFORMATION: PME-1 shRNA

<400> SEQUENCE: 39
cccaggttaa atacagccca t                                          21

<210> SEQ ID NO 40
<211> LENGTH: 21
<212> TYPE: DNA
<213> ORGANISM: Artificial Sequence
<220> FEATURE:
<223> OTHER INFORMATION: PME-1 shRNA

<400> SEQUENCE: 40
gcttatccaa tctctttctt a                                          21
```